(12) United States Patent
Kho et al.

(10) Patent No.: US 11,790,686 B2
(45) Date of Patent: Oct. 17, 2023

(54) COMPOSITE PIEZOELECTRIC ELEMENT AND ELECTRONIC DEVICE HAVING THE SAME

(71) Applicant: LG Display Co., Ltd., Seoul (KR)

(72) Inventors: YuSeon Kho, Paju-si (KR); Yong-Su Ham, Paju-si (KR); YongWoo Lee, Paju-si (KR)

(73) Assignee: LG DISPLAY CO., LTD., Seoul (KR)

( * ) Notice: Subject to any disclaimer, the term of this patent is extended or adjusted under 35 U.S.C. 154(b) by 0 days.

(21) Appl. No.: 17/115,286

(22) Filed: Dec. 8, 2020

(65) Prior Publication Data

US 2021/0174046 A1 Jun. 10, 2021

(30) Foreign Application Priority Data

Dec. 9, 2019 (KR) .......................... 10-2019-0162932

(51) Int. Cl.
*H01L 41/08* (2006.01)
*G06V 40/13* (2022.01)
*G06F 3/16* (2006.01)
*G06F 3/01* (2006.01)
*A61B 5/1172* (2016.01)

(52) U.S. Cl.
CPC .......... *G06V 40/1306* (2022.01); *G06F 3/016* (2013.01); *G06F 3/16* (2013.01); *A61B 5/1172* (2013.01)

(58) Field of Classification Search
CPC ......... G06K 9/0002; G06F 3/016; G06F 3/16; G01L 9/0072; H04R 17/00; H04R 1/24; B06B 1/0622
USPC ......................................... 1/1; 310/334, 368
See application file for complete search history.

(56) References Cited

U.S. PATENT DOCUMENTS

| | | | |
|---|---|---|---|
| 6,278,224 B1* | 8/2001 | Sawada | B06B 1/0622 310/368 |
| 6,984,922 B1* | 1/2006 | Nagahara | H04R 17/00 310/334 |
| 2007/0182287 A1* | 8/2007 | Lukacs | B06B 1/0622 310/334 |
| 2018/0321784 A1* | 11/2018 | Park | G01L 9/0072 |
| 2020/0401777 A1* | 12/2020 | Won | H04R 1/24 |

FOREIGN PATENT DOCUMENTS

KR 10-2017-0053109 A 5/2017

* cited by examiner

*Primary Examiner* — Abdul-Samad A Adediran
(74) *Attorney, Agent, or Firm* — Morgan, Lewis & Bockius LLP

(57) ABSTRACT

A composite piezoelectric element and an electronic device having the same are disclosed, in which the composite piezoelectric element includes insulating films and piezoelectric bodies, which are alternately arranged, wherein the piezoelectric bodies may be categorized into general piezoelectric bodies used as at least one of a haptic actuator, a speaker actuator and a receiver actuator, and a finger scan recognition piezoelectric body for finger scan recognition.

22 Claims, 4 Drawing Sheets

_US 11,790,686 B2_

COMPOSITE PIEZOELECTRIC ELEMENT AND ELECTRONIC DEVICE HAVING THE SAME

CROSS-REFERENCE TO RELATED APPLICATIONS

This application claims the benefit of the Korean Patent Application No. 10-2019-0162932 filed on Dec. 9, 2019, which is hereby incorporated by reference as if fully set forth herein.

BACKGROUND

Technical Field

The present disclosure relates to a composite piezoelectric element embodied to perform various functions and an electronic device having the same.

Discussion of the Related Art

Recently, with high integration of an electronic device and development of advanced technologies, various functions are built in the electronic device.

For example, various functions such as a display function, a finger scan recognition function, a haptic function, and a sound output function are built in a portable electronic device (ex., cellular phone, etc.), and a piezoelectric body may be used for a finger scan recognition function, a haptic function, and a sound output function.

In the related art, since a device for performing each function is independently built in the electronic device, there are a lot of difficulties in miniaturization and slimness of the electronic device.

In this respect, various studies for integrating elements, which may commonly be used, among elements required to perform the functions, have been made. For example, studies for a film type piezoelectric body, which may commonly be used to perform various functions, have been made.

SUMMARY

Accordingly, embodiments of the present disclosure are directed to a composite piezoelectric element and an electronic device having the same that substantially obviates one or more of the problems due to limitations and disadvantages of the related art.

The present disclosure has been made in view of the above problems, and it is an object of the present disclosure to provide a film type composite piezoelectric element that may perform various functions such as a haptic function, a speaker function, a receiver function and a finger scan recognition function.

It is another object of the present disclosure to provide an electronic device having a film type composite piezoelectric element, which may perform various functions, to embody miniaturization and slimness.

Additional features and aspects will be set forth in the description that follows, and in part will be apparent from the description, or may be learned by practice of the inventive concepts provided herein. Other features and aspects of the inventive concepts may be realized and attained by the structure particularly pointed out in the written description, or derivable therefrom, and the claims hereof as well as the appended drawings.

In accordance with an aspect of the present disclosure, the above and other objects can be accomplished by the provision of a composite piezoelectric element comprising insulating films and piezoelectric bodies, which are alternately arranged, wherein the piezoelectric bodies may be categorized into general piezoelectric bodies used as at least one of a haptic actuator, a speaker actuator and a receiver actuator, and a finger scan recognition piezoelectric body for finger scan recognition.

All of the general piezoelectric bodies may be used as one of the haptic actuator, the speaker actuator and the receiver actuator.

The general piezoelectric bodies may be categorized into a plurality of groups, and the general piezoelectric bodies included in the respective groups may be used as different actuators.

Some of the general piezoelectric bodies may be used as actuators for one function, and the other general piezoelectric bodies may be used as actuators for composite functions.

The finger scan recognition piezoelectric body may include an ultrasonic oscillating piezoelectric body for oscillating ultrasonic waves for finger scan recognition, and an ultrasonic reception piezoelectric body for receiving a reflective signal reflected by ultrasonic waves oscillated from the ultrasonic oscillating piezoelectric body.

A first cavity may be formed in the ultrasonic oscillating piezoelectric body, and a second cavity may be formed in the ultrasonic reception piezoelectric body.

The first cavity may be formed at a depth for resonating a frequency of ultrasonic waves oscillated by the ultrasonic oscillating piezoelectric body, and the second cavity may be formed at a depth for resonating a frequency of ultrasonic waves received by the ultrasonic reception piezoelectric body.

The depth of the first cavity and the depth of the second cavity may be the same as or different from each other.

Respective depths of the first cavities formed in the ultrasonic oscillating piezoelectric body may be the same as or different from each other, and respective depths of the second cavities formed in the ultrasonic reception piezoelectric body may be the same as or different from each other.

A polymer material may further be formed in at least one of the first cavity and the second cavity.

A height of the polymer material formed in the first cavity and a height of the polymer material formed in the second cavity may be the same as or different from each other.

A polymer material may be formed in all of the first cavities formed in the ultrasonic oscillating piezoelectric body or formed in some of the first cavities, and may be formed in all of the second cavities formed in the ultrasonic reception piezoelectric body or formed in some of the second cavities.

Respective heights of the polymer materials formed in the first cavities may be the same as or different from each other, and respective heights of the polymer materials formed in the second cavities may be the same as or different from each other.

The composite piezoelectric element may further comprise at least one of a metal film formed in the second cavity and a metal plate covering the second cavity.

In accordance with another aspect of the present disclosure, the above and other objects can be accomplished by the provision of an electronic device comprising an ultrasonic sensor for finger scan recognition, and at least one or more actuators of a haptic actuator, a speaker actuator and a receiver actuator, wherein the ultrasonic sensor and the at least one or more actuators may constitute one composite piezoelectric element.

An ultrasonic oscillating piezoelectric body and an ultrasonic reception piezoelectric body, which constitute the ultrasonic sensor, may be provided in the composite piezoelectric element, and first and second cavities may respectively be formed in the ultrasonic oscillating piezoelectric body and the ultrasonic reception piezoelectric body.

A polymer material may further be formed in at least one of the first cavity and the second cavity.

A metal film may further be formed in the second cavity, and a metal plate may further be formed to cover the second cavity.

General piezoelectric bodies used as at least one of the haptic actuator, the speaker actuator and the receiver actuator may be provided in the composite piezoelectric element.

Some of the general piezoelectric bodies may be used as actuators for one function, and the other general piezoelectric bodies may be used as actuators for composite functions.

Details of the other embodiments are included in the detailed description and drawings.

If the composite piezoelectric element according to the embodiment of the present disclosure is used, all of various functions such as a haptic function, a speaker function, a receiver function and a finger scan recognition function may be embodied using one composite piezoelectric element.

Therefore, if the electronic device is embodied using the composite piezoelectric element according to the embodiment of the present disclosure, miniaturization and slimness of the electronic device may be embodied.

Also, since the composite piezoelectric element according to the embodiment of the present disclosure is embodied in the form of film, a position for the composite piezoelectric element is easily changed.

Also, since the composite piezoelectric element according to the embodiment of the present disclosure is embodied such that polymer insulating films and piezoelectric bodies are alternately arranged, a flexible composite piezoelectric element may be provided.

It is to be understood that both the foregoing general description and the following detailed description are exemplary and explanatory and are intended to provide further explanation of the inventive concepts as claimed.

BRIEF DESCRIPTION OF THE DRAWINGS

The accompanying drawings, which are included to provide a further understanding of the disclosure and are incorporated in and constitute a part of this application, illustrate embodiments of the disclosure and together with the description serve to explain various principles. In the drawings.

DETAILED DESCRIPTION

Figure 1:
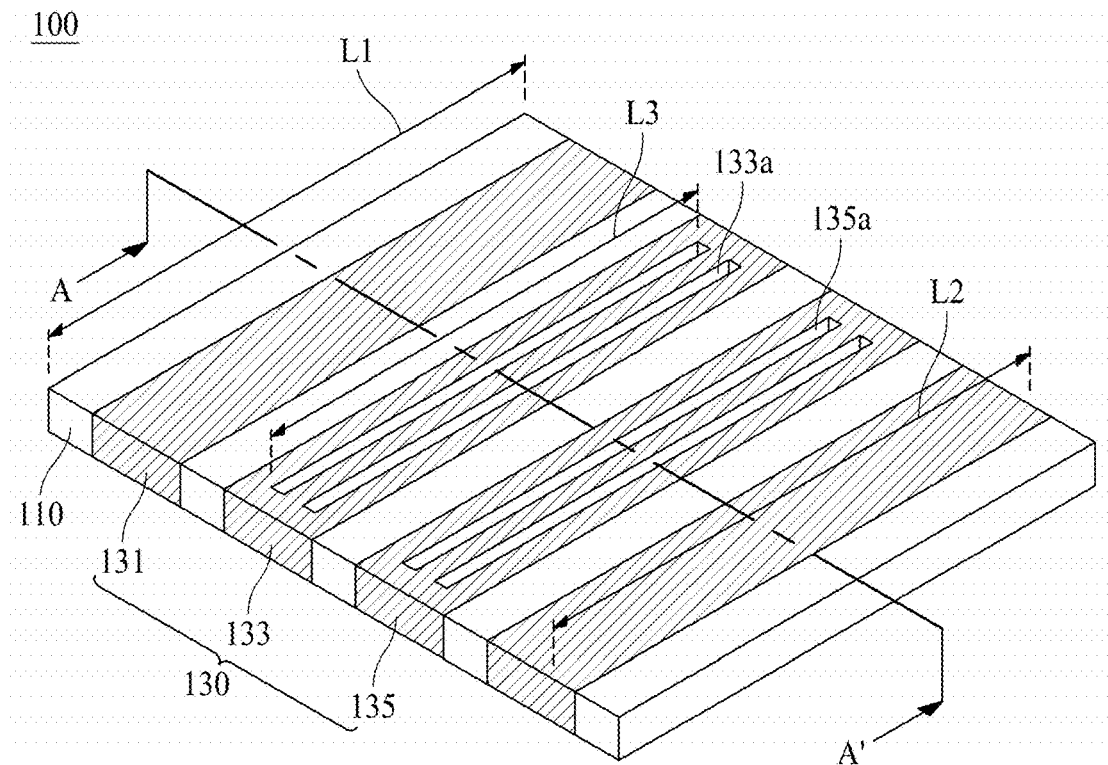
FIG. 1 is a view illustrating a composite piezoelectric element according to the first embodiment of the present disclosure.

Advantages and features of the present disclosure, and implementation methods thereof will be clarified through following embodiments described with reference to the accompanying drawings. The present disclosure may, however, be embodied in different forms and should not be construed as limited to the embodiments set forth herein. Rather, these embodiments are provided so that this disclosure will be thorough and complete, and will fully convey the scope of the present disclosure to those skilled in the art. Further, the present disclosure is only defined by scopes of claims.

A shape, a size, a ratio, an angle, and a number disclosed in the drawings for describing embodiments of the present disclosure are merely an example, and thus, the present disclosure is not limited to the illustrated details. Like reference numerals refer to like elements throughout the specification. In the following description, when the detailed description of the relevant known function or configuration is determined to unnecessarily obscure the important point of the present disclosure, the detailed description will be omitted. In a case where 'comprise', 'have', and 'include' described in the present specification are used, another part may be added unless 'only~' is used. The terms of a singular form may include plural forms unless referred to the contrary.

In construing an element, the element is construed as including an error range although there is no explicit description.

In describing a position relationship, for example, when the position relationship is described as 'upon~', 'above~', 'below~', and 'next to~', one or more portions may be arranged between two other portions unless 'just' or 'direct' is used.

It will be understood that, although the terms "first", "second", etc. may be used herein to describe various elements, these elements should not be limited by these terms. These terms are only used to distinguish one element from another. For example, a first element could be termed a second element, and, similarly, a second element could be termed a first element, without departing from the scope of the present disclosure.

In describing elements of the present disclosure, the terms "first", "second", etc. may be used. These terms are intended to identify the corresponding elements from the other elements, and basis, order, or number of the corresponding elements are not limited by these terms. The expression that an element is "connected" or "coupled" to another element should be understood that the element may directly be connected or coupled to another element but may directly be connected or coupled to another element unless specially mentioned, or a third element may be interposed between the corresponding elements.

Therefore, in the present disclosure, the display device may include a display device itself, such as LCM or the OLED module, and may also include a set device which is a final consumer device or an application product including the LCM or the OLED module.

For example, if a display panel is an organic light emitting display module (OLED) display panel, the display panel may include a plurality of gate and data lines, and pixels formed in intersection areas of the gate lines and the data lines. Also, the display panel may include an array substrate including a thin film transistor which is an element for selectively applying a voltage to each pixel, an organic light emitting diode (OLED) layer on the array substrate, and an encapsulation substrate arranged on the array substrate to cover the OLED layer.

The encapsulation substrate may protect the thin film transistor and the OLED layer from external impact, and may prevent water or oxygen from being permeated into the OLED layer. The layer formed on the array substrate may include an inorganic light emitting layer, for example, nano-sized material layer or quantum dot.

Features of various embodiments of the present disclosure may be partially or overall coupled to or combined with each other, and may be variously inter-operated with each other and driven technically as those skilled in the art can sufficiently understand. The embodiments of the present disclosure may be carried out independently from each other, or may be carried out together in co-dependent relationship.

Hereinafter, a composite piezoelectric element and an electronic device having the same according to the preferred embodiments of the present disclosure will be described in detail with reference to the accompanying drawings and examples.

Figure 2:
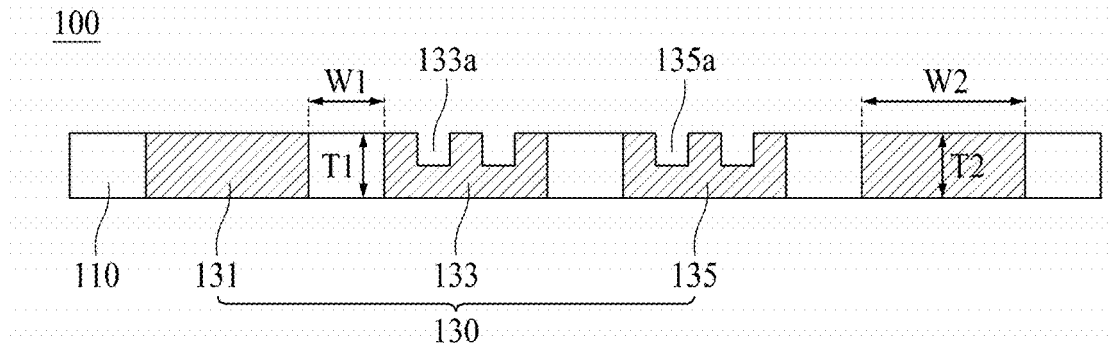
FIG. 2 is a cross-sectional view illustrating a composite piezoelectric element taken along line A-A' of FIG. 1.

FIG. 1 is a view illustrating a composite piezoelectric element according to the first embodiment of the present disclosure, and FIG. 2 is a cross-sectional view illustrating a composite piezoelectric element taken along line A-A' of FIG. 1.

Referring to FIGS. 1 and 2, the composite piezoelectric element 100 according to the first embodiment of the present disclosure may be provided in the form of a film of a predetermined thickness, and may include an insulating film 110 and a piezoelectric body 130, which are alternately arranged.

In this embodiment, the insulating film 110 and the piezoelectric body 130 are arranged in one direction (left and right direction based on drawing), but the arrangement structure of the insulating film 110 and the piezoelectric body 130 may be changed in various ways.

The composite piezoelectric element 100 may be embodied to be used for various purpose of uses. For example, the composite piezoelectric element 100 may be embodied to be used as a haptic actuator, a speaker actuator, a receiver actuator, a finger scan recognition actuator, etc., but the composite piezoelectric element 100 is not limited to this embodiment.

In order that the composite piezoelectric element 100 may be used for various purpose of uses, the piezoelectric body 130 may be formed to have different properties depending on purpose of uses, for example, may be formed to generate waves of different wavelengths.

The insulating film 110, for example, may be formed of a plate shape having a predetermined thickness, and for example, a soluble polymer material (ex., polymer matrix) may be used as the insulating film 110. If the insulating film 110 is formed of a soluble polymer material, a flexible composite piezoelectric element 100 may be manufactured.

A length L1, a thickness T1 and a width W1 of the insulating film 110 may be determined in various ways depending on a purpose of use of the composite piezoelectric element 100, specifications and structure of an electronic device to which the composite piezoelectric element 100 is applied, etc.

The piezoelectric body 130 may be formed of a rectangular plate shape having a predetermined thickness, for example, a piezoelectric ceramic. The piezoelectric body 130 may be formed of a piezoelectric material such as PZT(Pb, Zr, Ti), NKN(Na, K, Nb), and BNT(Bi, Na, Ti).

The piezoelectric body 30 may be formed of various piezoelectric materials, and may include barium titanate, lead titanate, lead zirconate titanate, potassium niobate, lithium niobate, lithium tantalate, sodium tungstate, zinc oxide, potassium sodium niobate, bismuth ferrite, sodium niobate, bismuth titanate, etc. However, the piezoelectric body 30 may be formed of fluoride polymer or a copolymer thereof.

A length L2, a thickness T2 and a width W2 of the piezoelectric body 30 may be determined in various ways depending on a purpose of use of the composite piezoelectric element 100, specifications and structure of an electronic device to which the composite piezoelectric element 100 is applied, etc.

The length L2, the thickness T2 and the width W2 of the piezoelectric body 130 may be equal to the length L1, the thickness T1 and the width W1 of the insulating film 110 but may be different from at least one or more of a length L, a thickness T and a width W in accordance with the embodiment.

Hereinafter, the piezoelectric body 130 will be described by being categorized into a general piezoelectric body 131 and finger scan recognition piezoelectric bodies 133 and 135. The number, shape and arrangement structure of the general piezoelectric body 131 and the finger scan recognition piezoelectric bodies 133 and 135 may be changed in various ways in consideration of details related to types and purpose of uses of the electronic device to which the composite piezoelectric element 100 is applied, a purpose of use of the composite piezoelectric element 100, etc.

The general piezoelectric body 131 may be used as a haptic actuator, a speaker actuator or a receiver actuator.

In accordance with the embodiment, the piezoelectric body 130 may be used as an actuator for one purpose of use, or may be used as an actuator for two purpose of uses.

For example, one general piezoelectric body 131 may be used as any one of the haptic actuator, the speaker actuator and the receiver actuator.

Alternatively, one general piezoelectric body 131 may be used as two or more of the haptic actuator, the speaker actuator and the receiver actuator.

In accordance with the embodiment, all of general piezoelectric bodies 131 may be used for one purpose of use, or may be used for different purpose of uses by being categorized into some groups to be used for different purpose of uses.

For example, all of general piezoelectric bodies 131 constituting the composite piezoelectric element 100 may be used as any one of the haptic actuator, the speaker actuator, and the receiver actuator.

Alternatively, a first group of the general piezoelectric body 131 constituting the composite piezoelectric element 100 may be used as an actuator (ex., haptic actuator) for a first purpose of use, a second group may be used as an actuator (ex., speaker actuator), and a third group may be used as an actuator (ex., receiver actuator) for a third purpose of use.

Although the above description has been based on that the general piezoelectric body 131 is categorized into three groups, the number of the general piezoelectric bodies 131 may be determined depending on a purpose of use of the composite piezoelectric element 100.

In accordance with the embodiment, some of general piezoelectric bodies 131 constituting the composite piezoelectric element 100 may be used for one purpose of use, and the other general piezoelectric bodies 131 may be used for composite purpose of uses.

For example, the first group of the general piezoelectric bodies 131 constituting the composite piezoelectric element 100 may be used as the speaker actuator, and the second group may be used as the haptic actuator and the receiver actuator.

The finger scan recognition piezoelectric body may include an ultrasonic oscillation piezoelectric body 133 for oscillating ultrasonic waves (ex., 10 MHz to 50 MHz) for finger scan recognition, and an ultrasonic reception piezoelectric body 135 for receiving a reflective signal reflected by ultrasonic waves oscillated from the ultrasonic oscillating piezoelectric body 133. Therefore, the finger scan recognition piezoelectric body may serve as an ultrasonic sensor.

In accordance with the embodiment, the ultrasonic oscillating piezoelectric body 133 may be vibrated to oscillate ultrasonic waves if a voltage is applied thereto under the control of a control device (not shown), and the ultrasonic reception piezoelectric body 135 may be vibrated by incident ultrasonic waves, and may receive an ultrasonic signal by a voltage difference generated by vibration.

In order to improve ultrasonic oscillating strength and reception sensitivity by using a resonant principle, cavities 133a and 135a may respectively be formed in the ultrasonic oscillating piezoelectric body 133 and the ultrasonic reception piezoelectric body 135, and may have a depth formed to resonate a unique frequency of a material of the piezoelectric bodies 133 and 135 and a unique frequency of a material in the cavities 133a and 135a in consideration of the unique frequencies.

The cavity 133a (first cavity) may be formed to reinforce ultrasonic oscillating strength of the ultrasonic oscillating piezoelectric body 133, and the cavity 135a (second cavity) may be formed to improve ultrasonic reception sensitivity of the ultrasonic reception piezoelectric body 135.

In accordance with the embodiment, the cavities 133a and 135a may be formed on an upper surface of the ultrasonic oscillating piezoelectric body 133 and an upper surface of the ultrasonic reception piezoelectric body 135 based on the corresponding drawing. That is, the cavity 133a may be formed on a surface, which is not in contact with the insulating film 110, among surfaces of the ultrasonic oscillating piezoelectric body 133, and the cavity 135a may be formed on a surface, which is not in contact with the insulating film 110, among surfaces of the ultrasonic reception piezoelectric body 135.

In accordance with the embodiment, the cavities 133a and 135a may be formed in, but not limited to, a rectangular cube having a predetermined depth, width and length. For example, the cavities 133a and 135a may be formed in a cube having a curved bottom surface.

In FIG. 2, the cavities 133a and 135a may be formed in each of the ultrasonic oscillating piezoelectric body 133 and the ultrasonic reception piezoelectric body 135 at a predetermined interval in pairs. However, the number of the cavities 133a and 135a formed in the ultrasonic oscillating piezoelectric body 133 and the ultrasonic reception piezoelectric body 135 is not limited to the example of FIG. 2.

In accordance with the embodiment, the number of the cavities 133a and 135a formed in the ultrasonic oscillating piezoelectric body 133 and the ultrasonic reception piezoelectric body 135 may be 1 or 3 or more.

In FIG. 2, the cavities 133a and 135a may be formed in each of the ultrasonic oscillating piezoelectric body 133 and the ultrasonic reception piezoelectric body 135 to have the same number. However, in accordance with the embodiment, the number of the cavities 133a formed in the ultrasonic oscillating piezoelectric body 133 may be different from the number of the cavities 235a formed in the ultrasonic reception piezoelectric body 135.

The number of the cavities 133a and 135a may be determined to improve ultrasonic oscillating strength and reception sensitivity in consideration of each width of the cavities 133a and 135a, each width of the ultrasonic oscillating piezoelectric body 133 and the ultrasonic reception piezoelectric body 135, etc.

In FIG. 2, the cavity 133a formed in the ultrasonic oscillating piezoelectric body 133 and the cavity 135a formed in the ultrasonic reception piezoelectric body 135 have the same width and depth, respective widths and depths of the cavities 133a formed in the ultrasonic oscillating piezoelectric body 133 are the same as each other, and respective widths and depths of the cavities 135a formed in the ultrasonic reception piezoelectric body 135 are the same as each other.

In accordance with the embodiment, at least one of each width and depth of the cavity 133a formed in the ultrasonic oscillating piezoelectric body 133 and each width and depth of the cavity 135a formed in the ultrasonic reception piezoelectric body 135 may be different from the other widths and depths.

In accordance with the embodiment, at least one of each width and depth of the cavities 133a formed in the ultrasonic oscillating piezoelectric body 133 may be different from the other width and depth, and at least one of each width and depth of the cavities 135a formed in the ultrasonic reception piezoelectric body 135 may be different from the other width and depth.

Each width and depth of the cavities 133a and 135a may be determined to improve ultrasonic oscillating strength and reception sensitivity in consideration of each width and depth of the ultrasonic oscillating piezoelectric body 133 and the ultrasonic reception piezoelectric body 135, etc.

In FIG. 2, the cavities 133a and 135a are formed in one direction at the same length. However, the lengths of the cavities 133a and 135a may be different from each other, and the cavities 133a and 135a may be formed in different directions.

In accordance with the embodiment, the length of the cavity 133a of the ultrasonic oscillating piezoelectric body 133 and the length of the cavity 135a of the ultrasonic reception piezoelectric body 135 may be different from each other.

In accordance with the embodiment, the respective lengths of the cavities 133a of the ultrasonic oscillating piezoelectric body 133 may be different from each other, and the respective lengths of the cavities 135a of the ultrasonic reception piezoelectric body 135 may be different from each other.

In accordance with the embodiment, a length direction of the cavity 133a of the ultrasonic oscillating piezoelectric body 133 and a length direction of the cavity 135a of the ultrasonic reception piezoelectric body 135 may be different from each other.

In accordance with the embodiment, the respective length directions of the cavities 133a of the ultrasonic oscillating piezoelectric body 133 may be different from each other, and the respective length directions of the cavities 135a of the ultrasonic reception piezoelectric body 135 may be different from each other.

Each length of the cavities 133a and 135a and each length direction of the cavities 133a and 135a may be determined to improve ultrasonic oscillating strength of the ultrasonic oscillating piezoelectric body 133 and ultrasonic reception sensitivity of the ultrasonic reception piezoelectric body 135.

Figure 3:
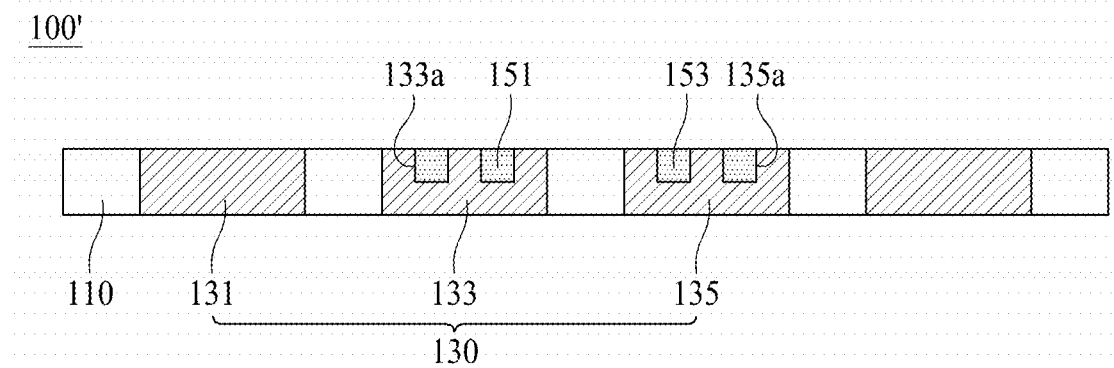
FIG. 3 is a cross-sectional view illustrating a composite piezoelectric element according to the second embodiment of the present disclosure.

FIG. 3 is a cross-sectional view illustrating a composite piezoelectric element according to the second embodiment of the present disclosure.

Hereinafter, among elements of a composite piezoelectric element 100' according to the second embodiment, the same elements as those of the composite piezoelectric element 100 according to the first embodiment will be omitted or described if necessary, and the same reference numerals will be given to the same elements as those of the composite piezoelectric element 100 according to the first embodiment.

The composite piezoelectric element 100' according to the second embodiment is different from the composite piezoelectric element 100 according to the first embodiment in that polymer materials 151 and 153 are formed in the cavities 133a of the ultrasonic oscillating piezoelectric body 133 and cavities 135a of the ultrasonic reception piezoelectric body 135.

In FIG. 3, the polymer materials 151 and 153 are all formed in the cavities 133a and 135a of the finger scan recognition piezoelectric bodies 133 and 135 but the present disclosure is not limited to the example of FIG. 3.

In accordance with the embodiment, the polymer material may be formed in only one of the cavity 133a of the ultrasonic oscillating piezoelectric body 133 and the cavity 135a of the ultrasonic reception piezoelectric body 135.

That is, the polymer material may be formed in only the cavity 133a of the ultrasonic oscillating piezoelectric body 133, or the polymer material may be formed in only the cavity 135a of the ultrasonic reception piezoelectric body 135.

In accordance with the embodiment, the polymer material may be formed in only some of the cavity 133a of the ultrasonic oscillating piezoelectric body 133, or the polymer material may be formed in only some of the cavity 135a of the ultrasonic reception piezoelectric body 135.

In FIG. 3, the polymer materials 151 and 153 are formed at the same height as that of the cavities 133a and 135a of the finger scan recognition piezoelectric bodies 133 and 135. That is, although the polymer materials 151 and 153 may be formed to fully fill the cavities 133a and 135a, the present disclosure is not limited to this example.

In accordance with the embodiment, the polymer material 151 may be formed in the cavity 133a of the ultrasonic oscillating piezoelectric body 133 to fully fill the cavity 133a, and the polymer material 153 may be formed in the cavity 135a of the ultrasonic reception piezoelectric body 135 to partially fill the cavity 135a.

In accordance with the embodiment, the polymer material 151 may be formed in some of the cavity 133a of the ultrasonic oscillating piezoelectric body 133 to fully fill the cavity 133a, and the polymer material 151 may be formed in the other of the cavity 133a to partially fill the cavity 133a.

In accordance with the embodiment, the polymer material 153 may be formed in some of the cavity 135a of the ultrasonic reception piezoelectric body 135 to fully fill the cavity 135a, and the polymer material 153 may be formed in the other of the cavity 135a to partially fill the cavity 135a.

Figure 4:
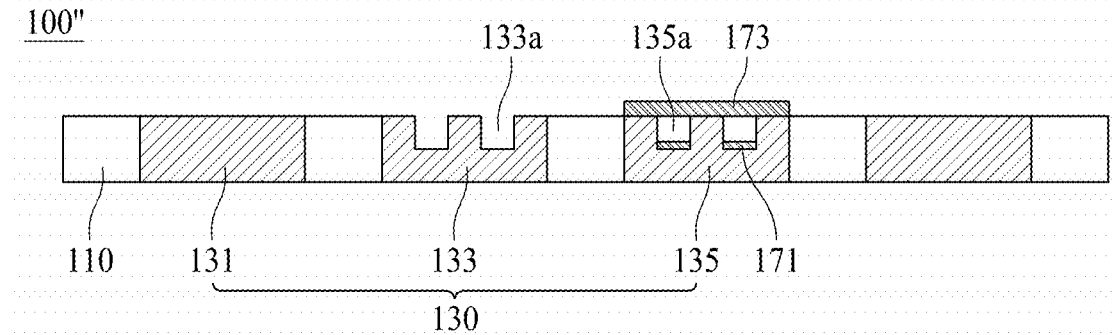
FIG. 4 is a cross-sectional view illustrating a composite piezoelectric element according to the third embodiment of the present disclosure.

FIG. 4 is a cross-sectional view illustrating a composite piezoelectric element according to the third embodiment of the present disclosure.

Hereinafter, among elements of a composite piezoelectric element 100" according to the third embodiment, the same elements as those of the composite piezoelectric element 100 according to the first embodiment will be omitted or described if necessary, and the same reference numerals will be given to the same elements as those of the composite piezoelectric element 100 according to the first embodiment.

The composite piezoelectric element 100" according to the third embodiment is different from the composite piezoelectric element 100 according to the first embodiment in that a metal film 171 is formed in the cavity 135a of the ultrasonic reception piezoelectric body 135, and a metal plate 173 covering the cavity 135a is formed above the ultrasonic reception piezoelectric body 135.

At this time, the metal film 171 and the metal plate 173 may be made of a material that may enhance ultrasonic reception efficiency, for example, metal having high sound impedance.

In this way, if the metal film 171 is formed in the cavity 135a of the ultrasonic reception piezoelectric body 135 and the metal plate 173 is formed to cover the cavity 135a provided with the metal film 171, ultrasonic waves entering the cavity 135a may be reflected/re-reflected in the cavity 135a by the metal film 171 and the metal plate 173 and thus maintained in the cavity 135a for a certain time period, whereby ultrasonic reception efficiency may be enhanced.

In FIG. 4, the metal film 171 is formed all of the cavity 135a of the ultrasonic reception piezoelectric body 35. However, the metal film 171 may be formed in only some of the cavity 135a.

In accordance with the embodiment, if an element that may serve as the metal plate 173 is arranged above the cavity 135a of the ultrasonic reception piezoelectric body 135, the metal plate 173 may be omitted.

In FIG. 4, the metal film 171 is formed in all of the cavity 135a of the ultrasonic reception piezoelectric body 135. However, the metal film 171 may be formed in only some of the cavity 135a.

In FIG. 4, the metal films 171 respectively formed in the cavities 135a of the ultrasonic reception piezoelectric body 135 have the same thickness. However, the metal film 171 respectively formed in the cavities 135a of the ultrasonic reception piezoelectric body 135 may have different thicknesses.

In FIG. 4, one metal plate 173 is formed to cover all of the cavities 135a. However, a plurality of metal plates 173 may be formed to individually cover the cavities 135a.

In accordance with the embodiment, the metal film 171 and the metal plate 173 may be formed to correspond to each other. That is, the metal plate 173 may be formed to cover the cavity 135a provided with the metal film 171.

Figure 5:
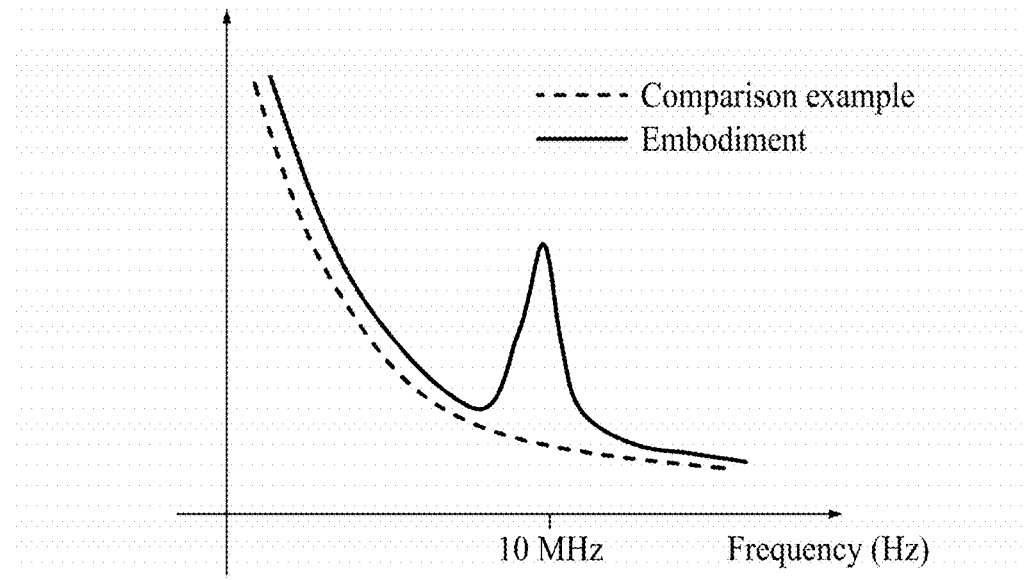
FIG. 5 is a view illustrating a comparison graph of ultrasonic oscillation strength in an ultrasonic oscillation piezoelectric body provided with cavities and an ultrasonic oscillation piezoelectric body provided with no cavity.

FIG. 5 is a view illustrating a comparison graph of ultrasonic oscillation strength in an ultrasonic oscillation piezoelectric body provided with cavities and an ultrasonic oscillation piezoelectric body provided with no cavity.

The graph of FIG. 5 shows ultrasonic oscillating strength in an embodiment of an ultrasonic oscillating piezoelectric body provided with cavities to improve oscillating strength for a signal of 10 MHz, wherein various frequencies intended to improve oscillating strength may be determined through a structure change of the cavity formed in the ultrasonic oscillating piezoelectric body.

For experiment, ultrasonic oscillating piezoelectric bodies having the same property may be used as the ultrasonic oscillating piezoelectric body of the embodiment and the ultrasonic oscillating piezoelectric body of a comparison example, wherein two cavities are formed in the ultrasonic oscillating piezoelectric body of the embodiment at a depth of 113 μm, and no cavity is formed in the ultrasonic oscillating piezoelectric body of the comparison example.

As noted in FIG. 5, oscillating strength of ultrasonic waves oscillated from the ultrasonic oscillating piezoelectric body provided with cavities is stronger than oscillating strength of ultrasonic waves oscillated from the ultrasonic oscillating piezoelectric body provided with no cavity.

In this way, the cavities may be formed in the ultrasonic oscillating piezoelectric body to reinforce oscillating strength of the ultrasonic waves oscillated by the ultrasonic oscillating piezoelectric body.

Figure 6:
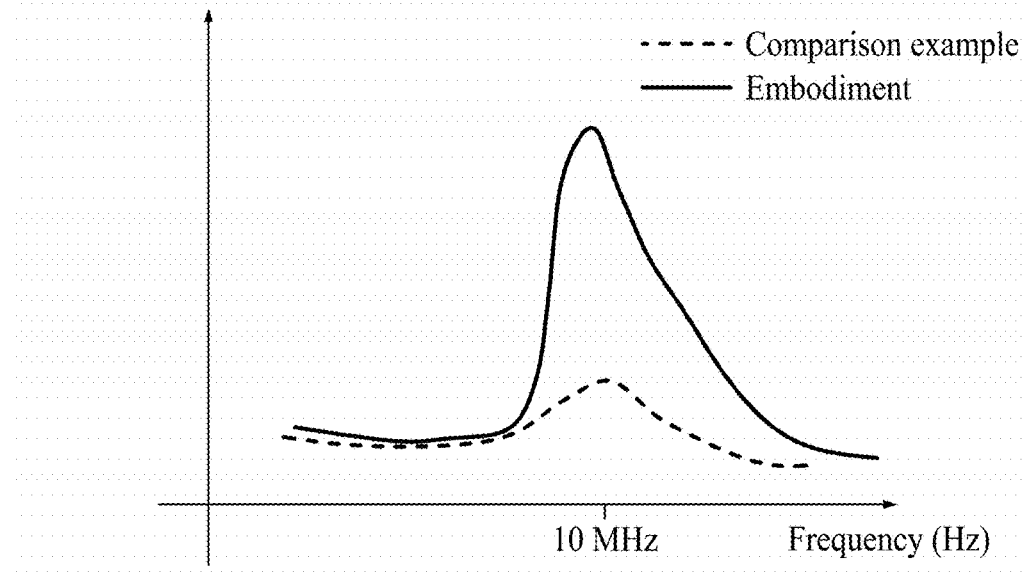
FIG. 6 is a view illustrating a comparison graph of ultrasonic reception sensitivity in an ultrasonic reception piezoelectric body provided with cavities and an ultrasonic reception piezoelectric body provided with no cavity.

FIG. 6 is a view illustrating a comparison graph of ultrasonic reception sensitivity in an ultrasonic reception piezoelectric body provided with cavities and an ultrasonic reception piezoelectric body provided with no cavity.

The graph of FIG. 6 shows ultrasonic reception sensitivity in an embodiment of an ultrasonic reception piezoelectric body provided with cavities to improve reception sensitivity for a signal of 10 MHz, wherein various frequencies intended to improve reception sensitivity may be determined through a structure change of the cavity formed in the ultrasonic reception piezoelectric body.

For experiment, ultrasonic reception piezoelectric bodies having the same property may be used as the ultrasonic reception piezoelectric body of the embodiment and the ultrasonic reception piezoelectric body of a comparison example, wherein two cavities are formed in the ultrasonic reception piezoelectric body of the embodiment at a depth of 9 μm, and no cavity is formed in the ultrasonic reception piezoelectric body of the comparison example.

As noted in FIG. 6, reception sensitivity of ultrasonic waves received by the ultrasonic reception piezoelectric body provided with cavities is stronger than reception sensitivity of ultrasonic waves received by the ultrasonic reception piezoelectric body provided with no cavity.

In this way, the cavities may be formed in the ultrasonic reception piezoelectric body to improve reception sensitivity of the ultrasonic waves received by the ultrasonic reception piezoelectric body.

Figure 7:
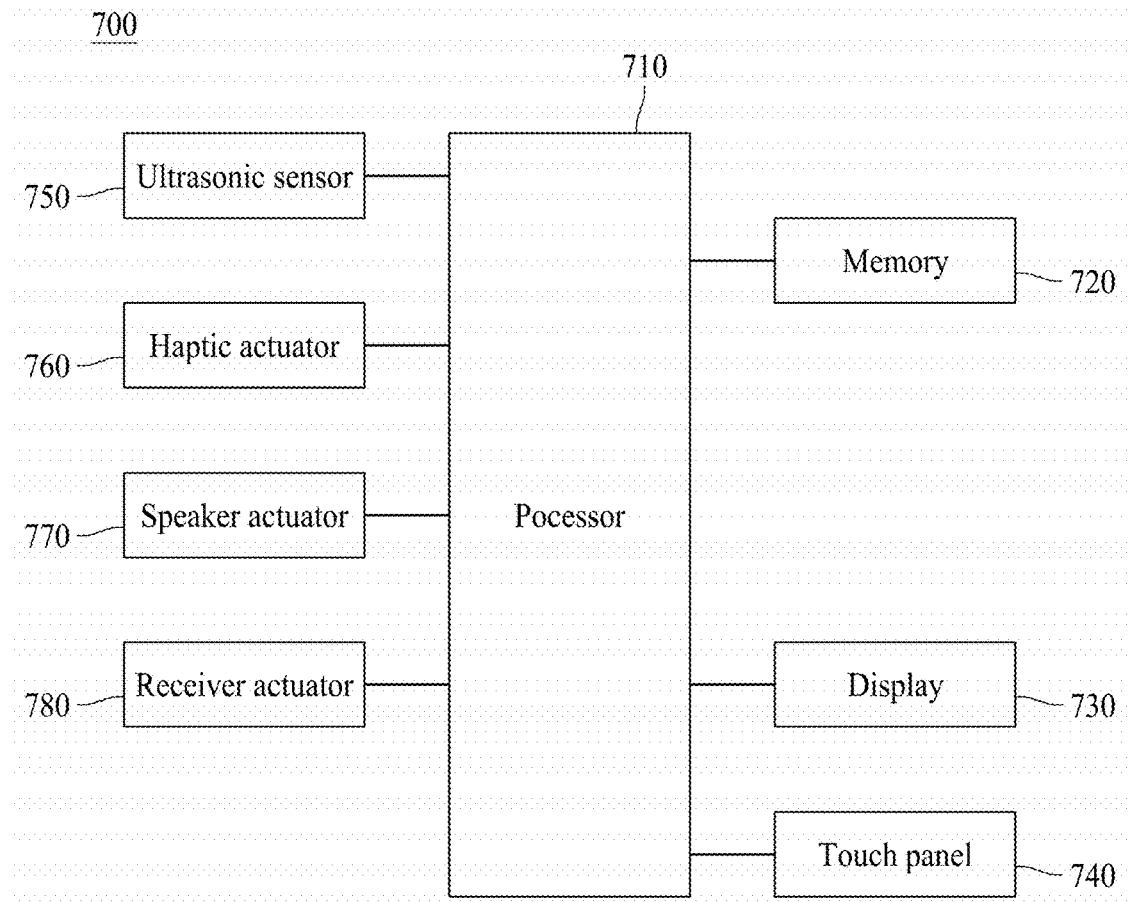
FIG. 7 is a block view illustrating an example of an electronic device provided with a composite piezoelectric element of the present disclosure.
Figure 8:
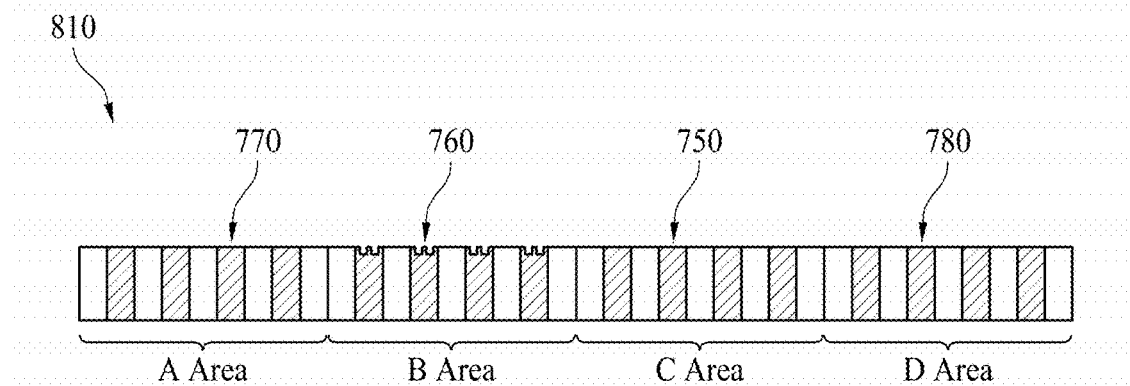
FIG. 8 is a cross-sectional view illustrating an example of a composite piezoelectric element provided in FIG. 7.

FIG. 7 is a block view illustrating an example of an electronic device provided with a composite piezoelectric element of the present disclosure, and FIG. 8 is a cross-sectional view illustrating an example of a composite piezoelectric element provided in FIG. 7.

The electronic device 700 according to the embodiment of the present disclosure, for example, may be, but not limited to, a smart phone, a tablet PC, a mobile phone, a video phone, an electronic reader, a desk top PC, a laptop PC, a netbook computer, a medical device, a camera, or a wearable device.

Referring to FIGS. 7 and 8, the electronic device 700 of FIG. 7 may include a processor 710, a memory 720, a display 730, a touch panel 740, an actuator 750, and an ultrasonic sensor 760, but is not limited thereto. The elements of the electronic device 700 are not limited to the embodiment of FIG. 7, and at least one of the elements may be omitted or another elements may additionally be provided.

The processor 710 may include one or more of a central processing unit, an application processor and a communication processor. For example, the processor 710 may execute computation or data processing for control and/or communication of at least one another element of the electronic device 700.

The memory 720 may include a volatile and/or non-volatile memory. For example, the memory 720 may store software and/or program used to execute a command and/or data, operation or function related to at least one another element of the electronic device 700.

The display 730 may display various contents (ex., text, image, video, icon and/or symbol, etc.), and for example, may be formed of any one of, but not limited to, a liquid crystal display (LCD), a light-emitting diode (LED) display, an organic light-emitting diode (OLED) display, a micro-electromechanical system (MEMS) display, and an electronic paper display.

The touch panel 740 may recognize a contact point touched based on a user's touch input signal (for example, touch or proximity) and measure a position value of a touch input. The touch panel 740 may be embodied in an add-on type arranged on the display panel 730 or an on-cell type or in-cell type inserted into the display 730. The touch panel 740 may be embodied in a resistive type, a capacitive type, an electromagnetic induction type, an optical type, etc.

The ultrasonic sensor 750 may include an ultrasonic oscillating piezoelectric body for oscillating ultrasonic waves if a voltage is applied thereto under the control of the processor 710, and an ultrasonic reception piezoelectric body for receiving reflective waves returning from the oscillated ultrasonic waves reflected by an external object (ex., user's hand or finger) touched an upper surface of the display 710, converting the reflective waves into electric signals and transferring body information (ex., finger scan data) corresponding to the external object to the processor 710.

The ultrasonic oscillating piezoelectric body and the ultrasonic reception piezoelectric body may be the ultrasonic oscillating piezoelectric body 133 and the ultrasonic reception piezoelectric body 135, which are described with reference to FIGS. 1 to 4. The ultrasonic sensor 750 may be formed in a certain area (area C) of the composite piezoelectric element 800 as shown in FIG. 8.

The haptic actuator 760 may be provided to provide a user with a haptic feedback (ex., vibration) in accordance with a signal applied under the control of the processor 710, and may be formed in a certain area (area B) of the composite piezoelectric element 800 as shown in FIG. 8.

The speaker actuator 770 may be provided to generate sound in accordance with a signal applied under the control of the processor 710, and may be formed in a certain area (area A) of the composite piezoelectric element 800 as shown in FIG. 8.

The receiver actuator 780 may be provided to receive a call in accordance with a signal applied under the control of the processor 710, and may be formed in a certain area (area D) of the composite piezoelectric element 800 as shown in FIG. 8.

In this way, the ultrasonic sensor 750, the haptic actuator 760, the speaker actuator 770 and the receiver actuator 780 may be formed in the composite piezoelectric element 800, whereby one composite piezoelectric element 800 may operate as an actuator for various functions.

Although FIG. 8 illustrates that the composite piezoelectric element 800 is partitioned by a plurality of areas (area A, area B, area C and area D), and each of the ultrasonic sensor 750, the haptic actuator 760, the speaker actuator 770 and the receiver actuator 780 is formed in one area, one actuator may be used for various functions as described with reference to FIGS. 1 to 4.

Although not shown in FIGS. 7 and 8, a film type thin film for protecting and supporting the composite piezoelectric element 800 may be arranged at upper and lower portions of the composite piezoelectric element 800.

It will be apparent to those skilled in the art that the present disclosure described above is not limited by the above-described embodiments and the accompanying drawings and that various substitutions, modifications, and variations can be made in the present disclosure without departing from the spirit or scope of the disclosures. Consequently, the scope of the present disclosure is defined by the accompanying claims, and it is intended that all variations or modifications derived from the meaning, scope, and equivalent concept of the claims fall within the scope of the present disclosure.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

It will be apparent to those skilled in the art that various modifications and variations can be made in the composite piezoelectric element and the electronic device having the same of the present disclosure without departing from the technical idea or scope of the disclosure. Thus, it is intended that the present disclosure cover the modifications and variations of this disclosure provided they come within the scope of the appended claims and their equivalents.

What is claimed is:

1. A composite piezoelectric element, comprising:
    insulating films and piezoelectric bodies, which are alternately arranged,
    wherein the piezoelectric bodies are categorized into general piezoelectric bodies used as at least one of a haptic actuator, a speaker actuator, and a receiver actuator, and piezoelectric bodies used as an ultrasonic sensor,
    wherein the piezoelectric bodies used as the ultrasonic sensor include:
        an ultrasonic oscillating piezoelectric body configured to oscillate ultrasonic waves and having a first cavity; and
        an ultrasonic reception piezoelectric body configured to receive a reflective signal reflected of ultrasonic waves oscillated from the ultrasonic oscillating piezoelectric body, the ultrasonic reception piezoelectric body having a second cavity different from the first cavity, and
    wherein the first cavity is formed in the ultrasonic oscillating piezoelectric body, and the second cavity is formed in the ultrasonic reception piezoelectric body.

2. The composite piezoelectric element of claim 1, wherein all of the general piezoelectric bodies are used as one of the haptic actuator, the speaker actuator and the receiver actuator.

3. The composite piezoelectric element of claim 1, wherein the general piezoelectric bodies are categorized into a plurality of groups, and the general piezoelectric bodies included in respective groups among the plurality of groups are used as different actuators.

4. The composite piezoelectric element of claim 1, wherein some of the general piezoelectric bodies are used as actuators for one function, and one or more others of the general piezoelectric bodies are used as actuators for composite functions.

5. The composite piezoelectric element of claim 1, wherein the first cavity is formed at a depth for resonating a frequency of ultrasonic waves oscillated by the ultrasonic oscillating piezoelectric body, and the second cavity is formed at a depth for resonating a frequency of ultrasonic waves received by the ultrasonic reception piezoelectric body.

6. The composite piezoelectric element of claim 1, wherein a depth of the first cavity and a depth of the second cavity are equal to or different from each other.

7. The composite piezoelectric element of claim 1, wherein the first cavity includes a plurality of first cavities formed in the ultrasonic oscillating piezoelectric body,
    wherein the second cavity includes a plurality of second cavities formed in the ultrasonic reception piezoelectric body, and
    wherein depths of the plurality of first cavities are equal to or different from each other, and depths of the plurality of second cavities are equal to or different from each other.

8. The composite piezoelectric element of claim 1, wherein a polymer material is further formed in at least one of the first cavity and the second cavity.

9. The composite piezoelectric element of claim 8, wherein a height of the polymer material formed in the first cavity and a height of the polymer material formed in the second cavity are equal to or different from each other.

10. The composite piezoelectric element of claim 7, wherein a polymer material is formed in all of the plurality of first cavities formed in the ultrasonic oscillating piezoelectric body or formed in some of the first cavities, and is formed in all of the plurality of second cavities formed in the ultrasonic reception piezoelectric body or formed in some of the second cavities.

11. The composite piezoelectric element of claim 10, wherein respective heights of the polymer materials formed in the plurality of first cavities are equal to or different from each other, and respective heights of the polymer materials formed in the plurality of second cavities are equal to or different from each other.

12. The composite piezoelectric element of claim 1, further comprising at least one of a metal film formed in the second cavity and a metal plate covering the second cavity.

13. The composite piezoelectric element of claim 1, wherein the ultrasonic sensor is configured to apply a finger scan recognition.

14. The electronic device of claim 1, wherein:
    the first cavity or the second cavity is disposed entirely within the at least one of the piezoelectric bodies without extending into another layer; and
    the first cavity or the second cavity has an opening at a top surface of the ultrasonic sensor and has a depth smaller than a thickness of the ultrasonic sensor, the ultrasonic sensor having no other cavity directly below the first cavity or the second cavity.

15. An electronic device, comprising:
an ultrasonic sensor; and
at least one or more actuators of a haptic actuator, a speaker actuator, and a receiver actuator,
wherein the ultrasonic sensor and the at least one or more actuators constitute one composite piezoelectric element including insulating films and piezoelectric bodies, which are alternately arranged,
wherein the piezoelectric bodies are categorized into general piezoelectric bodies used as the at least one or more actuators, and piezoelectric bodies used as the ultrasonic sensor,
wherein the piezoelectric bodies used as the ultrasonic sensor include a first cavity or a second cavity different from the first cavity,
wherein the general piezoelectric bodies do not include a cavity, and
wherein an ultrasonic oscillating piezoelectric body and an ultrasonic reception piezoelectric body, which constitute the piezoelectric bodies used as the ultrasonic sensor, are provided in the composite piezoelectric element, and the first cavity and the second cavity are respectively formed in the ultrasonic oscillating piezoelectric body and the ultrasonic reception piezoelectric body.

16. The electronic device of claim 15, wherein a polymer material is further formed in at least one of the first cavity and the second cavity.

17. The electronic device of claim 15, wherein a metal film is further formed in the second cavity, and a metal plate is further formed to cover the second cavity.

18. The electronic device of claim 15, wherein the general piezoelectric bodies are provided in the composite piezoelectric element.

19. The electronic device of claim 18, wherein some of the general piezoelectric bodies are used as actuators for one function, and one or more others of the general piezoelectric bodies are used as actuators for composite functions.

20. The electronic device of claim 15, wherein the ultrasonic sensor is configured to apply a finger scan recognition.

21. The electronic device of claim 15, wherein:
the ultrasonic oscillating piezoelectric body is configured to oscillate ultrasonic waves; and
the ultrasonic reception piezoelectric body is configured to receive a reflective signal reflected of ultrasonic waves oscillated from the ultrasonic oscillating piezoelectric body.

22. The electronic device of claim 15, wherein:
the first cavity or the second cavity is disposed entirely within the at least one of the piezoelectric bodies without extending into another layer; and
the first cavity or the second cavity has an opening at a top surface of the ultrasonic sensor and has a depth smaller than a thickness of the ultrasonic sensor, the ultrasonic sensor having no other cavity directly below the first cavity or the second cavity.

\* \* \* \* \*